United States Patent
Anglese

(10) Patent No.: US 12,310,685 B2
(45) Date of Patent: *May 27, 2025

(54) DRIVE MECHANISMS FOR SURGICAL INSTRUMENTS SUCH AS FOR USE IN ROBOTIC SURGICAL SYSTEMS

(71) Applicant: Covidien LP, Mansfield, MA (US)

(72) Inventor: Kurt J. Anglese, Lafayette, CO (US)

(73) Assignee: Covidien LP, Mansfield, MA (US)

(*) Notice: Subject to any disclaimer, the term of this patent is extended or adjusted under 35 U.S.C. 154(b) by 42 days.

This patent is subject to a terminal disclaimer.

(21) Appl. No.: 18/211,888

(22) Filed: Jun. 20, 2023

(65) Prior Publication Data
US 2023/0329809 A1    Oct. 19, 2023

Related U.S. Application Data

(63) Continuation of application No. 16/260,477, filed on Jan. 29, 2019, now Pat. No. 11,717,355.

(51) Int. Cl.
*A61B 34/30*      (2016.01)
*A61B 17/29*      (2006.01)
(Continued)

(52) U.S. Cl.
CPC .............. *A61B 34/30* (2016.02); *A61B 17/29* (2013.01); *A61B 34/71* (2016.02);
(Continued)

(58) Field of Classification Search
CPC ......... A61B 34/30; A61B 34/71; A61B 17/29; A61B 2034/305; A61B 2017/00398; A61B 2017/2926
See application file for complete search history.

(56) References Cited

U.S. PATENT DOCUMENTS

| 5,752,973 A | 5/1998 | Kieturakis |
|---|---|---|
| 5,792,135 A | 8/1998 | Madhani et al. |

(Continued)

FOREIGN PATENT DOCUMENTS

| CN | 102596087 A | 7/2012 |
|---|---|---|
| CN | 107249495 A | 10/2017 |

(Continued)

OTHER PUBLICATIONS

Second Chinese Office Action issued in corresponding Chinese Application No. 202010073327.7 dated May 11, 2024, 11 pages.

(Continued)

*Primary Examiner* — Michael F Peffley
*Assistant Examiner* — Bo Ouyang
(74) *Attorney, Agent, or Firm* — Carter, DeLuca & Farrell LLP

(57) ABSTRACT

A gearbox assembly and surgical instrument including the same. The gearbox assembly includes a drive gear including a round gear and a lead screw such that a rotational input to the round gear rotates the lead screw. A first hub is threadingly engaged about the lead screw such that rotation of the lead screw translates the first hub. A second hub is spaced-apart from the first hub and engaged with a drive rod. A compression spring is disposed between the hubs. When a force acting against the drive rod is below a threshold, the rotational input translates the first hub, compression spring, second hub, and drive rod. When the force is equal to or above the threshold, the rotational input translates the first hub and compresses the compression spring against the second hub to maintain the second hub and drive rod in position.

20 Claims, 18 Drawing Sheets

(51) Int. Cl.
*A61B 34/00* (2016.01)
*A61B 17/00* (2006.01)

(52) U.S. Cl.
CPC .............. *A61B 2017/00398* (2013.01); *A61B 2017/2926* (2013.01); *A61B 2034/305* (2016.02)

(56) References Cited

U.S. PATENT DOCUMENTS

| | | |
|---|---|---|
| 5,848,986 A | 12/1998 | Lundquist et al. |
| 6,132,368 A | 10/2000 | Cooper |
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,817,974 B2 | 11/2004 | Cooper et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,799,028 B2 | 9/2010 | Schechter et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,861,906 B2 | 1/2011 | Doll et al. |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,918,230 B2 | 4/2011 | Whitman et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,579,176 B2 | 11/2013 | Smith et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |

(56) References Cited

U.S. PATENT DOCUMENTS

| | | |
|---|---|---|
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Piolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |

(56) References Cited

U.S. PATENT DOCUMENTS

| | | |
|---|---|---|
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 11,717,355 B2 | 8/2023 | Anglese et al. |
| 2002/0099371 A1 | 7/2002 | Schulze et al. |
| 2002/0177842 A1 | 11/2002 | Weiss |
| 2003/0125734 A1 | 7/2003 | Mollenauer |
| 2003/0208186 A1 | 11/2003 | Moreyra |
| 2006/0022015 A1 | 2/2006 | Shelton et al. |
| 2006/0025811 A1 | 2/2006 | Shelton |
| 2007/0233052 A1 | 10/2007 | Brock |
| 2008/0015631 A1 | 1/2008 | Lee et al. |
| 2010/0274265 A1 | 10/2010 | Wingardner et al. |
| 2010/0292691 A1 | 11/2010 | Brogna |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2012/0310256 A1 | 12/2012 | Brisson |
| 2016/0242779 A1 | 8/2016 | Aranyi et al. |
| 2016/0303745 A1 | 10/2016 | Rockrohr |
| 2017/0367775 A1 | 12/2017 | Dachs, II et al. |
| 2018/0008338 A1* | 1/2018 | Kopp .................. A61B 18/1445 |
| 2018/0028271 A1* | 2/2018 | Rockrohr ............... A61B 34/35 |
| 2018/0049763 A1 | 2/2018 | Kappus et al. |
| 2018/0263717 A1 | 9/2018 | Kopp |

FOREIGN PATENT DOCUMENTS

| | | |
|---|---|---|
| CN | 107405173 A | 11/2017 |
| CN | 108289713 A | 7/2018 |
| CN | 108697478 A | 10/2018 |
| WO | 2017053698 A1 | 3/2017 |

OTHER PUBLICATIONS

Extended European Search Report issued in corresponding Appl. No. EP 20154025.9 dated Jun. 19, 2020 (8 pages).

Chinese Office Action issued in corresponding Chinese Application No. 202010073327.7 dated Jan. 22, 2024, 12 pages.

* cited by examiner

DRIVE MECHANISMS FOR SURGICAL INSTRUMENTS SUCH AS FOR USE IN ROBOTIC SURGICAL SYSTEMS

CROSS-REFERENCE TO RELATED APPLICATIONS

This application is a continuation of U.S. patent application Ser. No. 16/260,477, filed on Jan. 29, 2019, the entire contents of which are hereby incorporated herein by reference.

BACKGROUND

Technical Field

The present disclosure relates to surgical instruments and, more specifically, to drive mechanisms for surgical instruments such as, for example, for use in robotic surgical systems.

Background of Related Art

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be taken in determining how to utilize the available inputs provided by the robotic arm to achieve the desired functionality of the surgical instrument.

SUMMARY

As used herein, the term "distal" refers to the portion that is being described which is further from a surgeon, while the term "proximal" refers to the portion that is being described which is closer to a surgeon. The terms "about," "substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is a gearbox assembly for a surgical instrument. The gearbox assembly includes a drive gear, a first hub, a second hub, a drive rod, and a compression spring. The drive gear includes a round gear configured to receive a rotational input and a lead screw coupled to the round gear such that the rotational input to the round gear rotates the lead screw. The first hub is threadingly engaged about the lead screw such that rotation of the lead screw translates the first hub therealong. The second hub is spaced-apart from the first hub. The drive rod is engaged with the second hub. The compression spring is disposed between the first and second hubs. When a force acting against translation of the drive rod is below a threshold, the rotational input translates the first hub to, in turn, translate the compression spring to, in turn, translate the second hub and the drive rod. When the force acting against translation of the drive rod is equal to or above the threshold, the rotational input translates the first hub to, in turn, compress the compression spring against the second hub while the second hub and drive rod are maintained in position.

In an aspect of the present disclosure, an input gear disposed in meshed engagement with the round gear of the drive gear to provide the rotational input to the round gear.

In another aspect of the present disclosure, an external input is provided and an input shaft is operably coupled between the external input and the input gear such that rotational driving of the external input provides the rotational input to the round gear.

In another aspect of the present disclosure, the first hub is a distal hub and the second hub is a proximal hub. In such aspects, the external input may be disposed proximally of the proximal hub and the input gear may be disposed distally of the distal hub.

In yet another aspect of the present disclosure, the drive rod extends coaxially through at least one of or each of: the first hub, the second hub, the compression spring, or the drive gear.

In still another aspect of the present disclosure, the first and second hubs are coupled to one another to define a maximum distance therebetween. The compression spring is partially compressed when the first and second hubs define the maximum distance therebetween.

In still yet another aspect of the present disclosure, at least one guide bar is operably coupled between the first and second hubs. The guide bar(s) defines first and second rims configured to interact with first and second shoulders of the first and second hubs, respectively, to define the maximum distance between the first and second hubs.

In another aspect of the present disclosure, the first hub is moved towards the second hub when the compression spring is compressed against the second hub to reduce a distance between the first and second hubs.

In another aspect of the present disclosure, the drive rod is engaged with the second hub via a lock plate defining a keyhole.

Also provided in accordance with aspects of the present disclosure is a surgical instrument including a housing, a shaft extending distally from the housing, an end effector assembly extending distally from the shaft and including first and second jaw members at least the first of which is movable relative to the second from a spaced-apart position to an approximated position to grasp tissue therebetween, and a gearbox assembly disposed within the housing. The gearbox assembly may be configured similarly to any of the aspects detailed hereinabove or otherwise herein such that when a force acting against movement of at least the first jaw member towards the approximated position is below a threshold, the rotational input translates the first hub to, in turn, translate the compression spring to, in turn, translate the second hub and the drive rod to move at least the first jaw member towards the approximated position. When the force acting against movement of at least the first jaw member towards the approximated position is equal to or above the threshold, the rotational input translates the first hub to, in turn, compress the compression spring against the second hub while the second hub, the drive rod, and at least the first jaw member are maintained in position.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
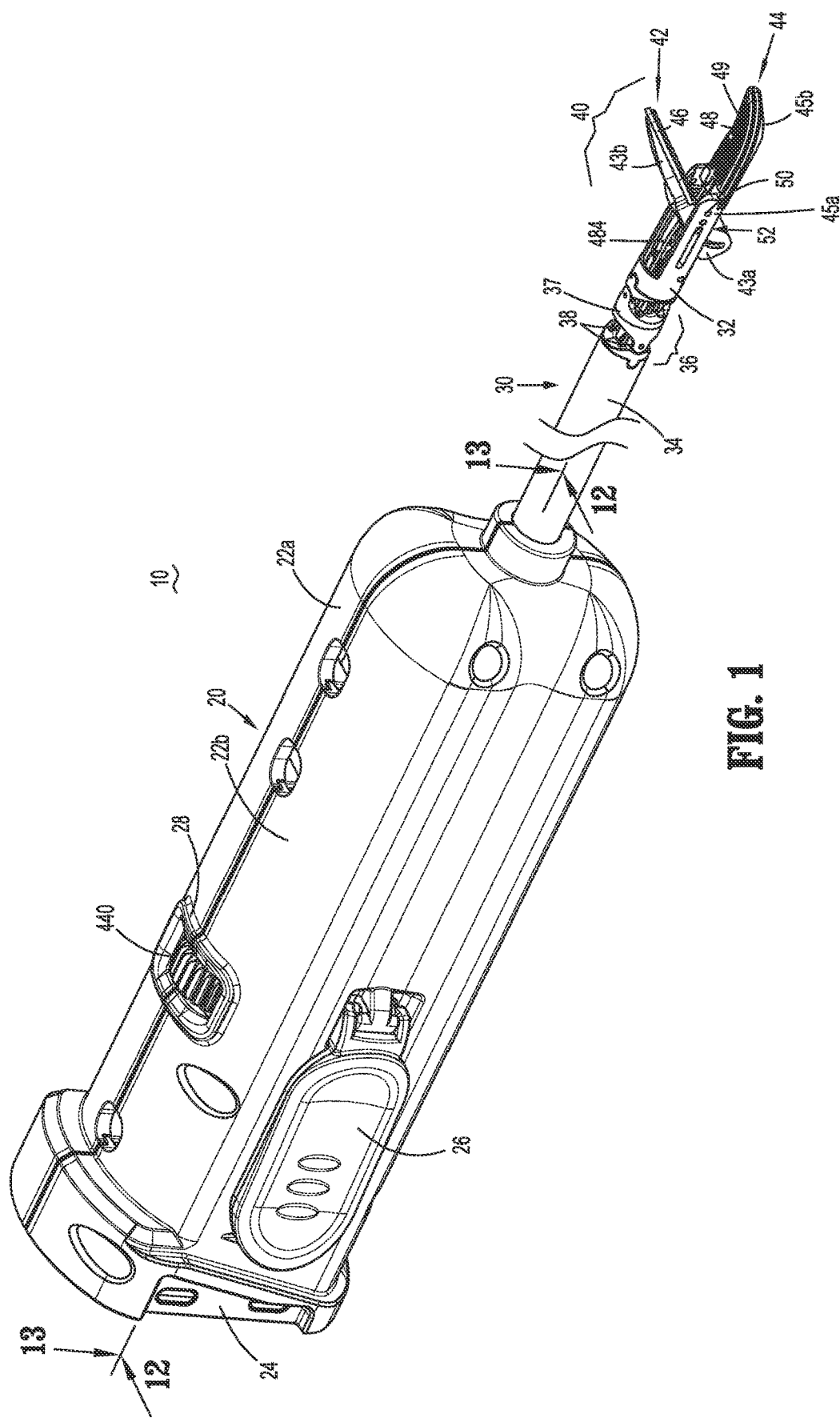
FIG. 1 is a perspective view of a surgical instrument provided in accordance with the present disclosure configured for mounting on a robotic arm of a robotic surgical system.
Figure 2A:
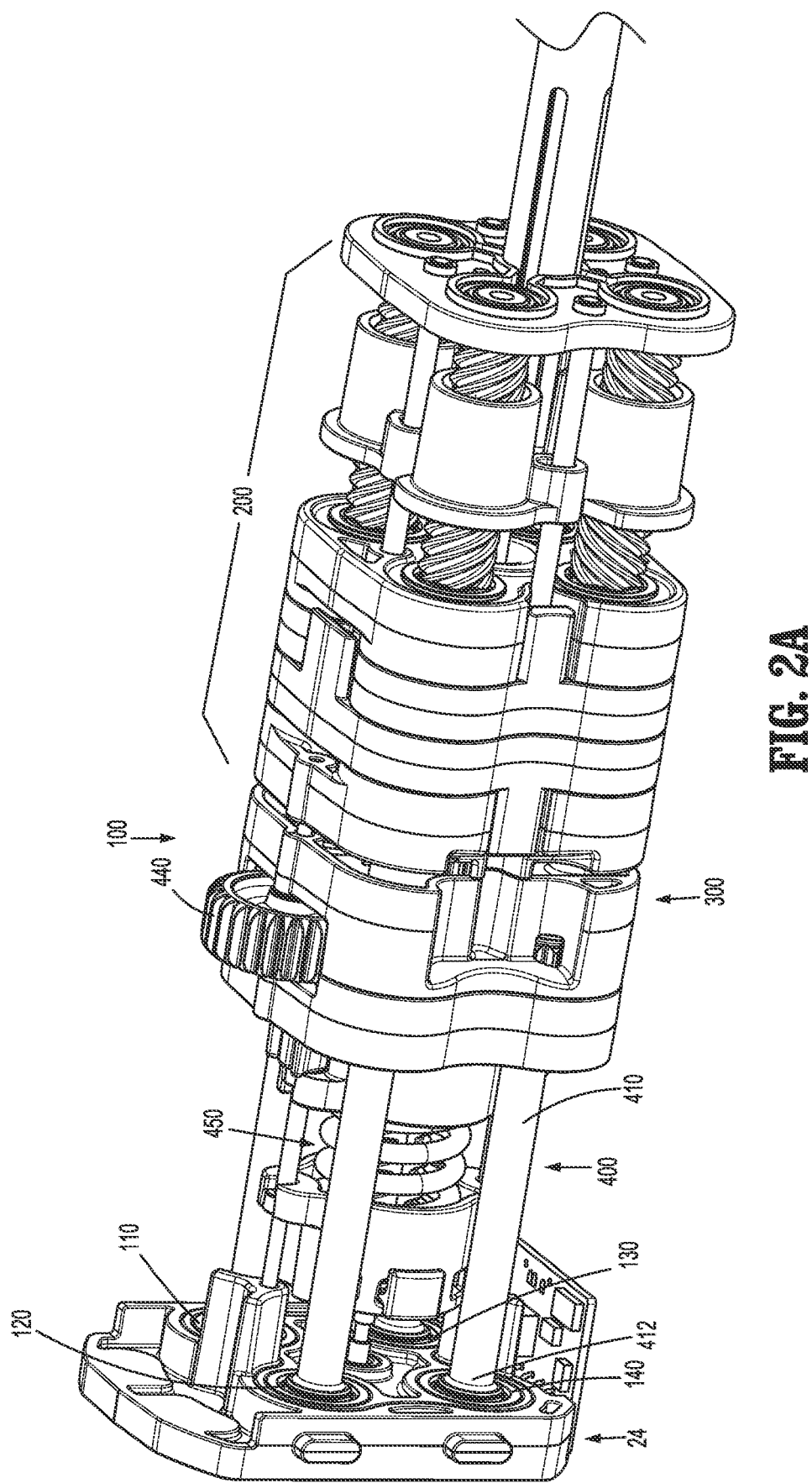
FIG. 2A is a front, perspective view of a proximal portion of the surgical instrument of FIG. 1 with an outer shell removed.
Figure 2B:
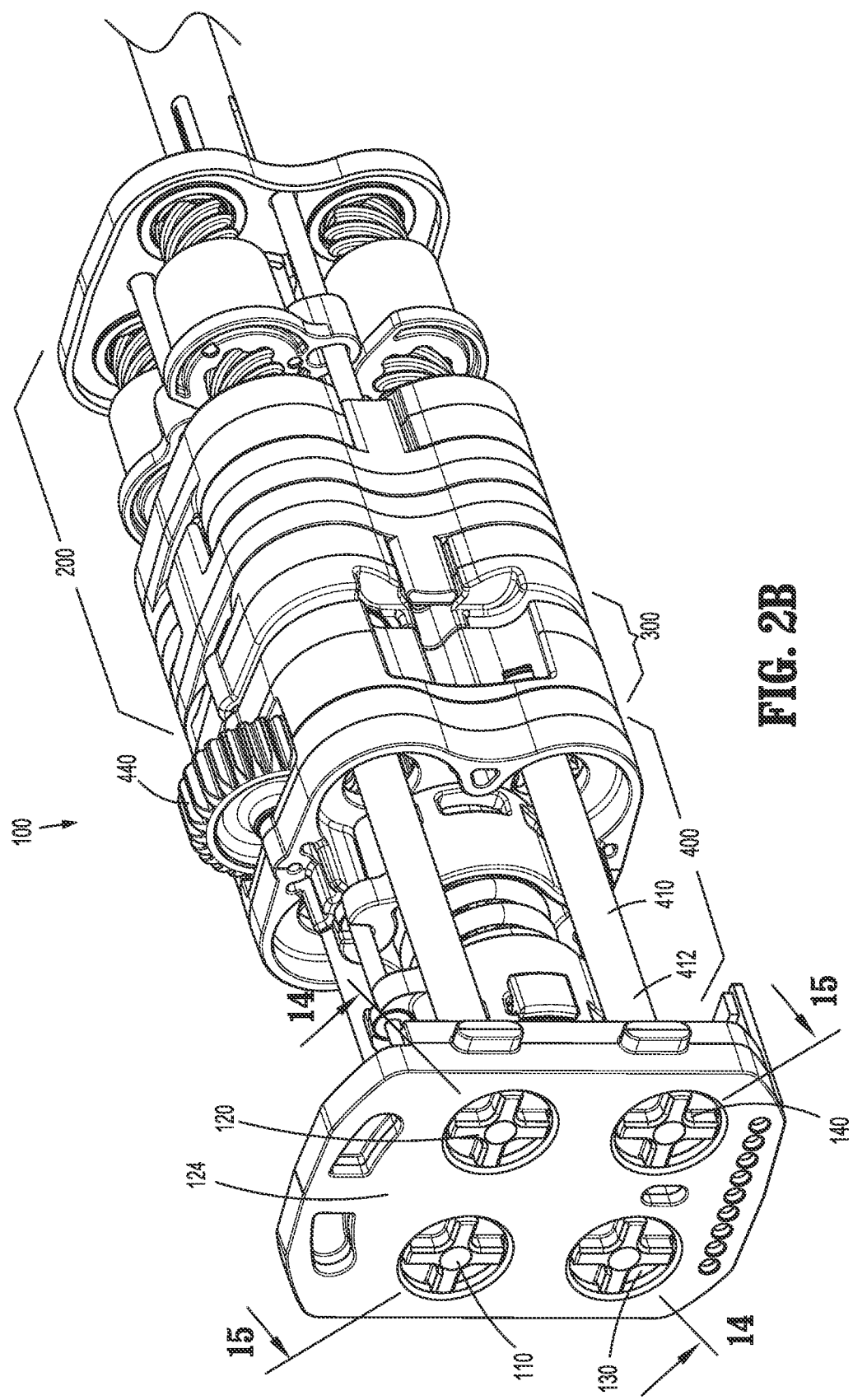
FIG. 2B is a rear, perspective view of the proximal portion of the surgical instrument of FIG. 1 with the outer shell removed.
Figure 3:
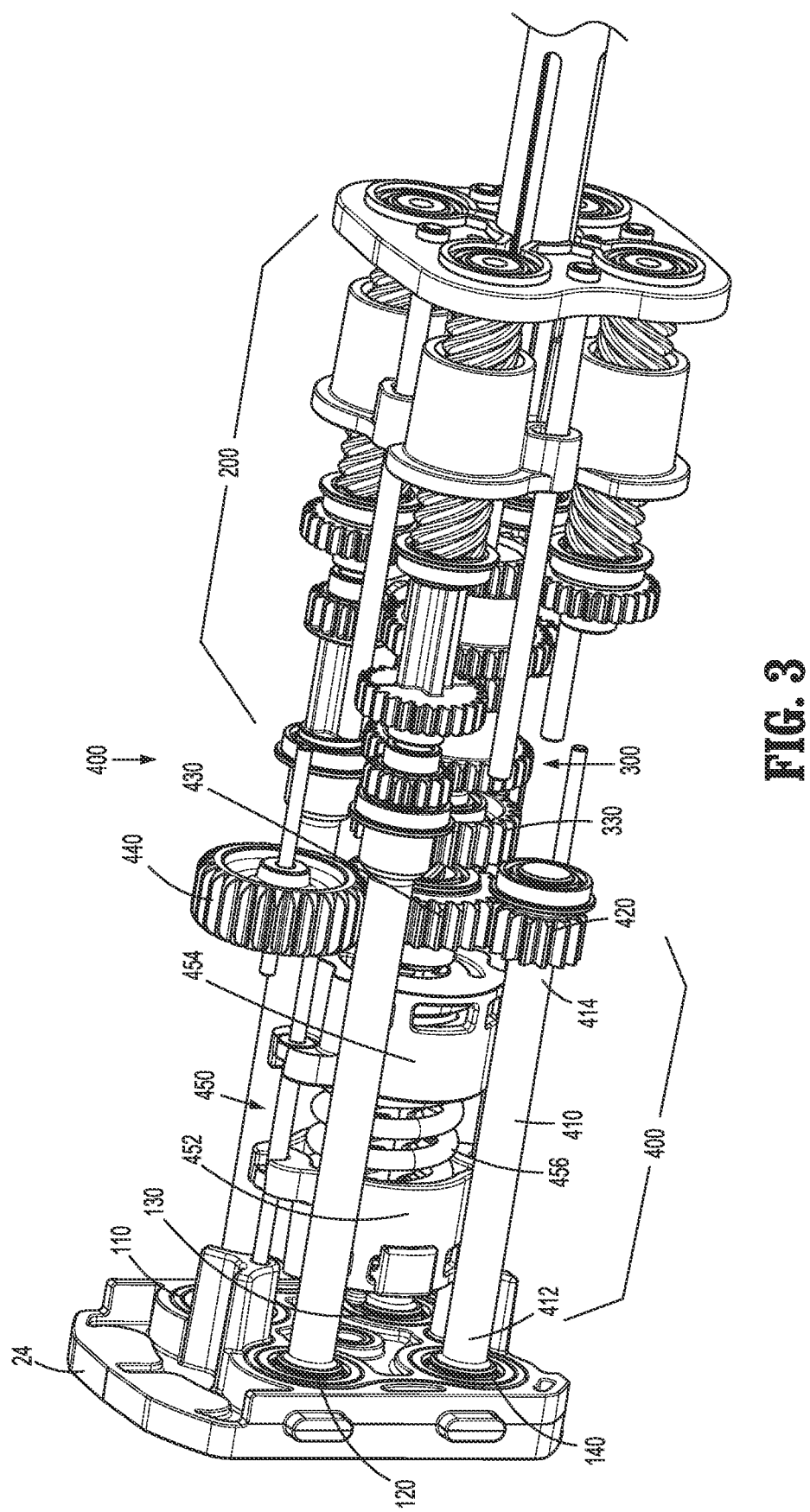
FIG. 3 is a front, perspective view of the proximal portion of the surgical instrument of FIG. 1 with the outer shell and additional internal components removed.
Figure 4:
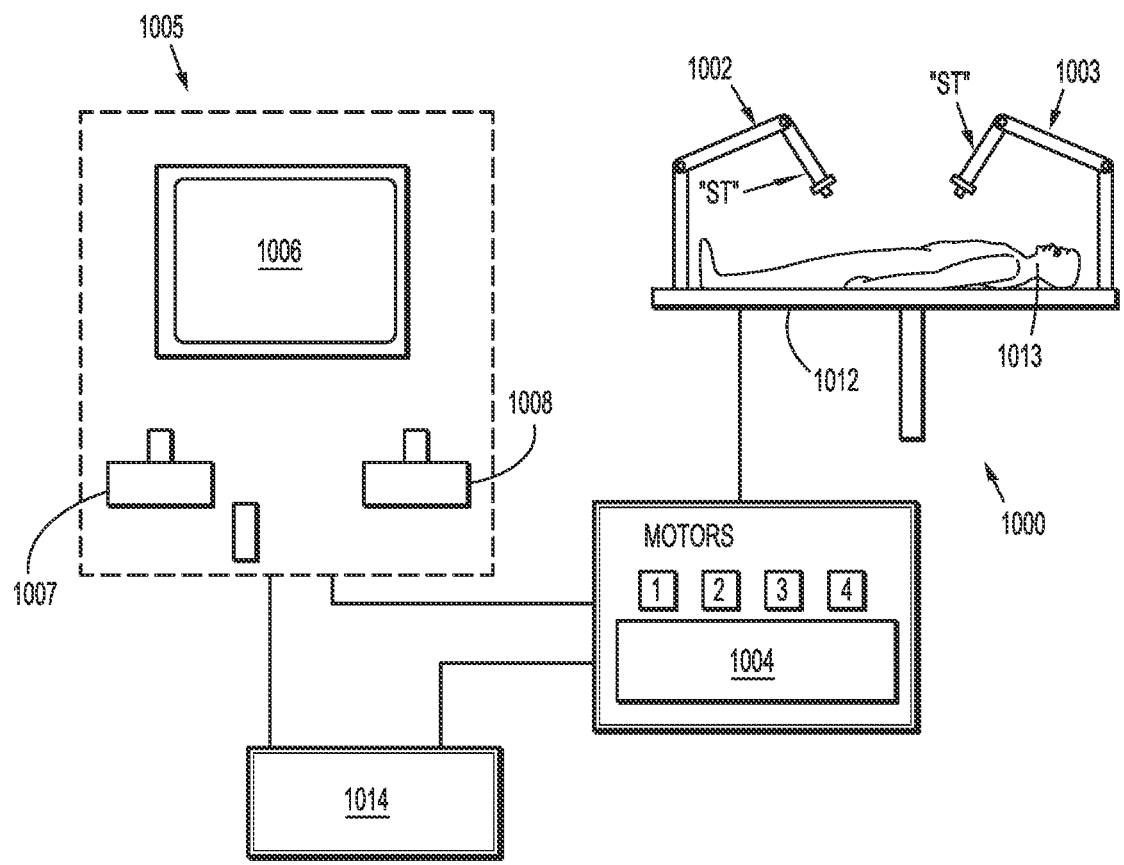
FIG. 4 is a schematic illustration of an exemplary robotic surgical system configured to releasably receive the surgical instrument of FIG. 1.

Referring to FIGS. 1-3, a surgical instrument 10 provided in accordance with the present disclosure generally includes a housing 20, a shaft 30 extending distally from housing 20, and end effector assembly 40 extending distally from shaft 30, and a gearbox assembly 100 disposed within housing 20 and operably associated with end effector assembly 40. Instrument 10 is detailed herein as an articulating electro-surgical forceps configured for use with a robotic surgical system, e.g., robotic surgical system 1000 (FIG. 4). However, the aspects and features of instrument 10 provided in accordance with the present disclosure, detailed below, are equally applicable for use with other suitable surgical instruments and/or in other suitable surgical systems.

With particular reference to FIG. 1, housing 20 of instrument 10 includes first and second body portion 22a, 22b and a proximal face plate 24 that cooperate to enclose gearbox assembly 100 therein. Proximal face plate 24 includes apertures defined therein through which inputs 110-140 of gearbox assembly 100 extend. A pair of latch levers 26 (only one of which is illustrated in FIG. 1) extending outwardly from opposing sides of housing 20 and enable releasable engagement of housing 20 with a robotic arm of a surgical system, e.g., robotic surgical system 1000 (FIG. 4). An aperture 28 defined through housing 20 permits thumbwheel 440 to extend therethrough to enable manual manipulation of thumbwheel 440 from the exterior of housing 20 to, as detailed below, permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extend through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation sub-assembly 200 of gearbox assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 are actuated in a similar manner while the lower pair of cables 38 are actuated in a similar manner relative to one another but an opposite manner relative to the upper pair of cables 38. With respect to yaw articulation, the right pair of cables 38 are actuated in a similar manner while the left pair of cables 38 are actuated in a similar manner relative to one another but an opposite manner relative to the right pair of cables 38.

Continuing with reference to FIG. 1, end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue "T" (FIGS. 20 and 22) between tissue-contacting surfaces 46, 48. As an alternative to this unilateral configuration, a bilateral configuration may be provided whereby both jaw members 42, 44 are pivotable relative to one another and distal segment 32 of shaft 30.

In embodiments, longitudinally-extending knife channels 49 (only knife channel 49 of jaw member 44 is illustrated; the knife channel of jaw member 42 is similarly configured) are defined through tissue-contacting surfaces 46, 48, respectively, of jaw members 42, 44. In such embodiments, a knife assembly including a knife tube 62 (FIGS. 12-15) extending from housing 20 through shaft 30 to end effector assembly 40 and a knife blade (not shown) disposed within end effector assembly 40 between jaw members 42, 44 is provided to enable cutting of tissue "T" (FIGS. 20 and 22) grasped between tissue-contacting surfaces 46, 48 of jaw members 42, 44, respectively. Knife tube 62 (FIGS. 12-15) is operably coupled to a knife drive sub-assembly 300 of gearbox assembly 100 (FIGS. 2A-2B) at a proximal end thereof to enable selective actuation thereof to, in turn, reciprocate the knife blade (not shown) between jaw members 42, 44 to cut tissue "T" (FIGS. 20 and 22) grasped between tissue-contacting surfaces 46, 48.

Referring still to FIG. 1, a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with a jaw drive sub-assembly 400 of gearbox assembly 100 (FIGS. 2A-2B) to enable selective actuation of end effector assembly 40 to grasp tissue "T" (FIGS. 20 and 22) therebetween and apply a closure force within an appropriate jaw closure force range, as detailed below.

Tissue-contacting surfaces 46, 48 of jaw members 42, 44, respectively, are at least partially formed from an electrically conductive material and are energizable to different potentials to enable the conduction of electrical energy through tissue "T" (FIGS. 20 and 22) grasped therebetween, although tissue-contacting surfaces 46, 48 may alternatively be configured to supply any suitable energy, e.g., thermal, microwave, light, ultrasonic, ultrasound, etc., through tissue "T" (FIGS. 20 and 22) grasped therebetween for energy-based tissue treatment. Instrument 10 defines a conductive pathway (not shown) through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue "T" (FIGS. 20 and 22) grasped between tissue-contacting surfaces 46, 48.

With additional reference to FIGS. 2A, 2B, and 3, as noted above, gearbox assembly 100 is disposed within housing 20 and includes an articulation sub-assembly 200, a knife drive sub-assembly 300, and a jaw drive sub-assembly 400. Articulation sub-assembly 200 is operably coupled between first and second inputs 110, 120, respectively, of gearbox assembly 100 and articulation cables 38 (FIG. 1) such that, upon receipt of appropriate inputs into first and/or second inputs 110, 120, articulation sub-assembly 200 manipulates cables 38 (FIG. 1) to articulate end effector assembly 40 in a desired direction, e.g., to pitch and/or yaw end effector assembly 40.

Knife drive sub-assembly 300 is operably coupled between third input 130 of gearbox assembly 100 and knife tube 62 (FIGS. 12-15) such that, upon receipt of appropriate input into third input 130, knife drive sub-assembly 300 manipulates knife tube 62 (FIGS. 12-15) to reciprocate the knife blade (not shown) between jaw members 42, 44 to cut tissue "T" (FIGS. 20 and 22) grasped between tissue-contacting surfaces 46, 48.

Jaw drive sub-assembly 400, as detailed below, is operably coupled between fourth input 140 of gearbox assembly 100 and drive rod 484 such that, upon receipt of appropriate input into fourth input 140, jaw drive sub-assembly 400 pivots jaw members 42, 44 between the spaced-apart and approximated positions to grasp tissue "T" (FIGS. 20 and 22) therebetween and apply a closure force within an appropriate closure force range.

Gearbox assembly 100 is configured to operably interface with a robotic surgical system 1000 (FIG. 4) when instrument 10 is mounted on robotic surgical system 1000 (FIG. 4), to enable robotic operation of gearbox assembly 100 to provide the above-detailed functionality. That is, robotic surgical system 1000 (FIG. 4) selectively provides inputs to inputs 110-140 of gearbox assembly 100 to articulate end effector assembly 40, grasp tissue "T" (FIGS. 20 and 22) between jaw members 42, 44, and/or cut tissue "T" (FIGS. 20 and 22) grasped between jaw members 42, 44. However, it is also contemplated that gearbox assembly 100 be configured to interface with any other suitable surgical system, e.g., a manual surgical handle, a powered surgical handle, etc. For the purposes herein, robotic surgical system 1000 (FIG. 4) is generally described.

Turning to FIG. 4, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and mounted device which may be, for example, a surgical tool "ST." One or more of the surgical tools "ST" may be instrument 10 (FIG. 1), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

With reference to FIGS. 5-7 and 12-19, jaw drive subassembly 400 of gearbox assembly 100 is shown generally including an input shaft 410, an input gear 420, a drive gear 430, a thumbwheel 440, a spring force assembly 450, and a drive rod assembly 480.

Input shaft 410 includes a proximal end portion 412 operably coupled to fourth input 140 and a distal end portion 414 having input gear 420 engaged thereon such that rotational input provided to fourth input 140 drives rotation of input shaft 410 to, thereby, drive rotation of input gear 420. Input gear 420 is disposed in meshed engagement with round gear 432 of drive gear 430 such that rotation of input gear 420, e.g., in response to a rotational input provided at fourth input 140, effects rotation of drive gear 430 in an opposite direction (see FIG. 16). Thumbwheel 440 is also disposed in meshed engagement with round gear 432 of drive gear 430 such that rotation of thumbwheel 440 effects rotation of drive gear 430 in an opposite direction, thus enabling manual driving of drive gear 430 via manipulation of thumbwheel 440 (see FIG. 16).

Figure 11:
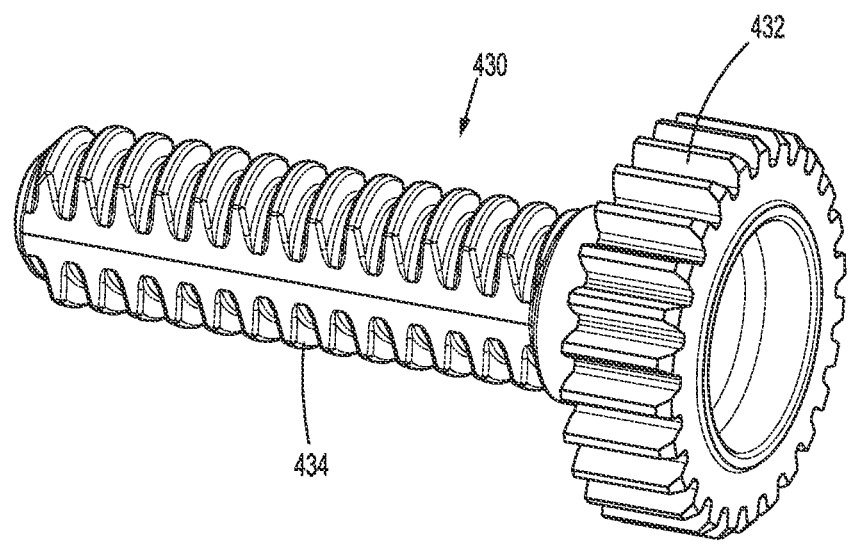
FIG. 11 is an enlarged, perspective view of the area of detail "11" in FIG. 7.
Figure 12:
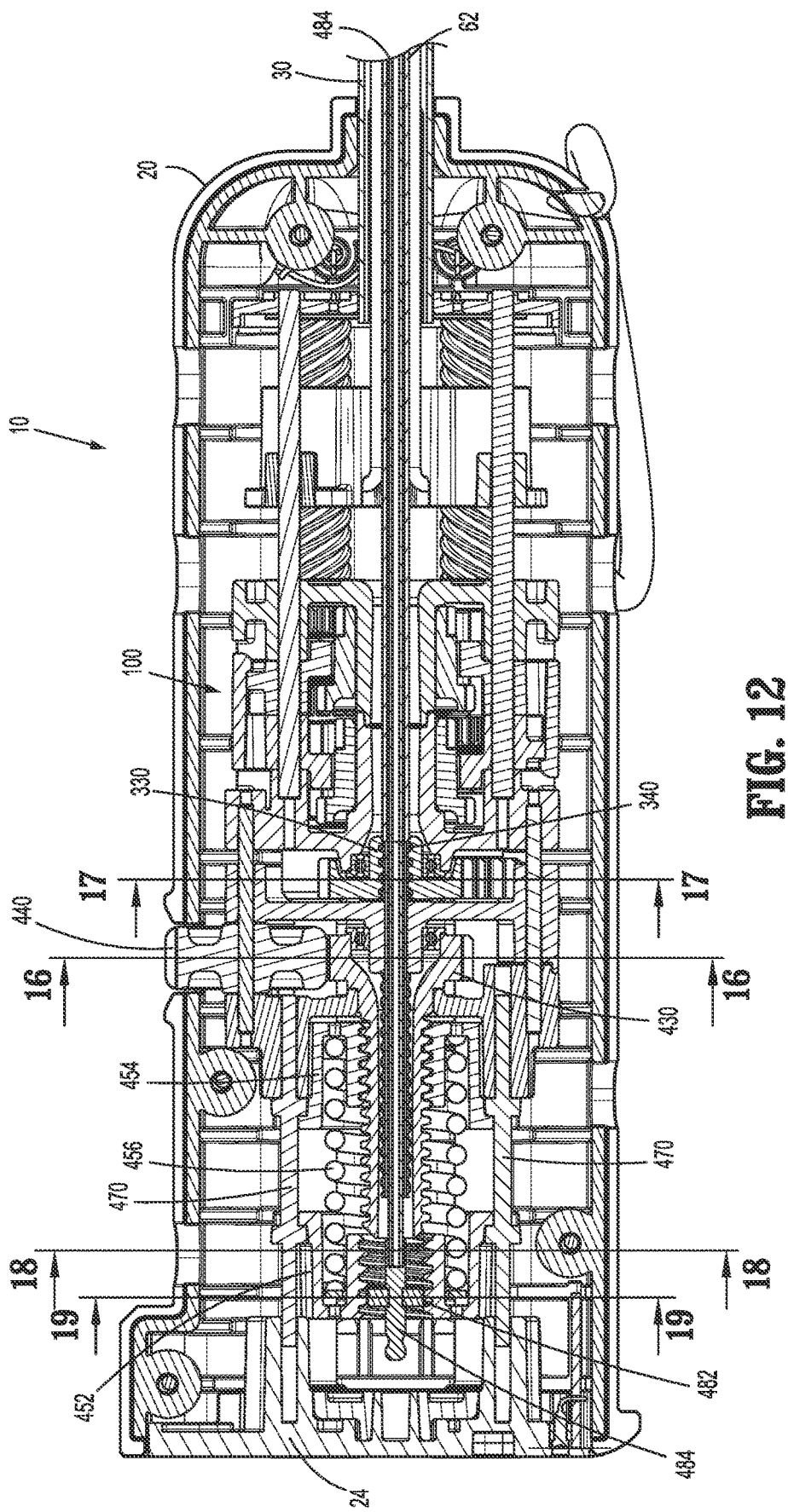
FIG. 12 is a longitudinal, cross-sectional view taken along section line "12-12" of FIG. 1.
Figure 13:
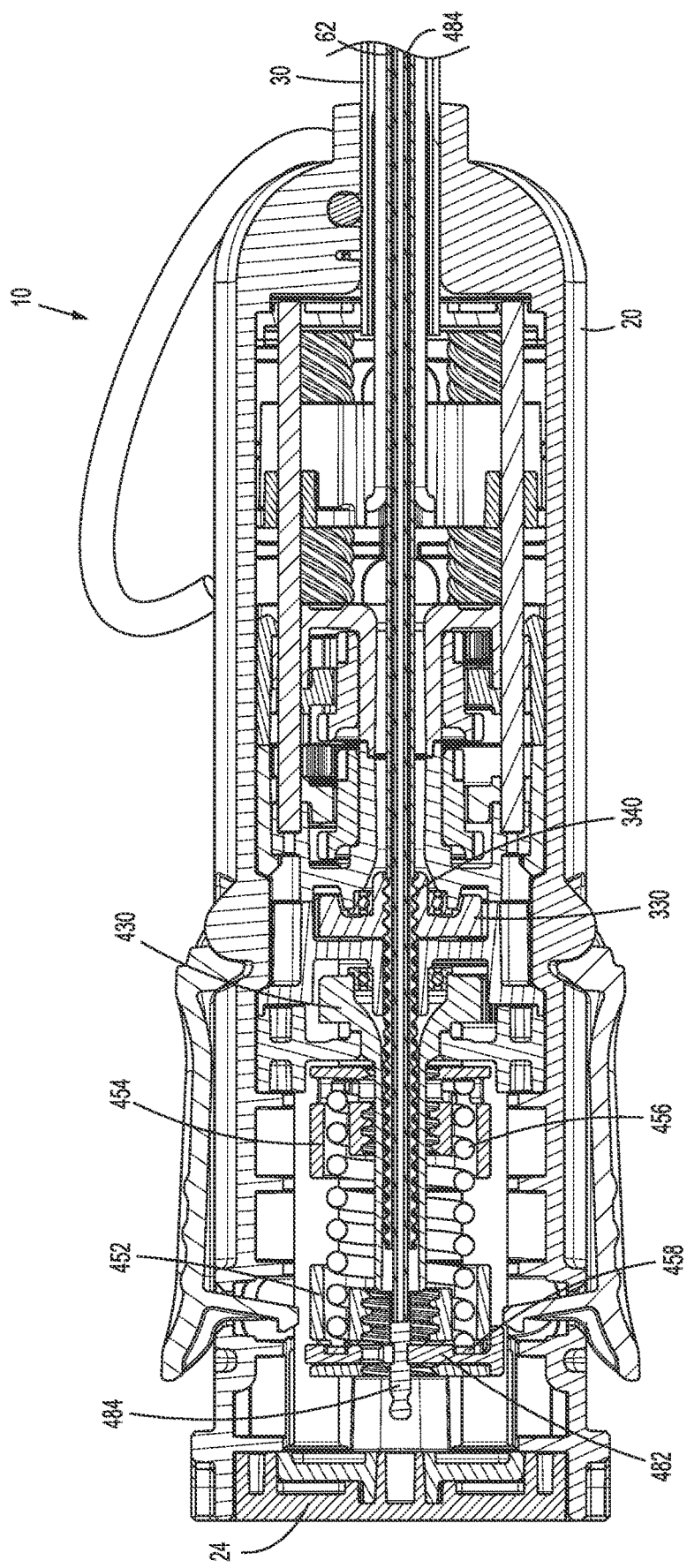
FIG. 13 is a longitudinal, cross-sectional view taken along section line "13-13" of FIG. 1.

Also referring to FIG. 11, drive gear 430, as noted above, includes a round gear 432. Drive gear 430 further includes a lead screw 434 fixedly engaged, e.g., monolithically formed, with round gear 432 such that rotation of round gear 432 effects similar rotation of lead screw 434.

Figure 8:
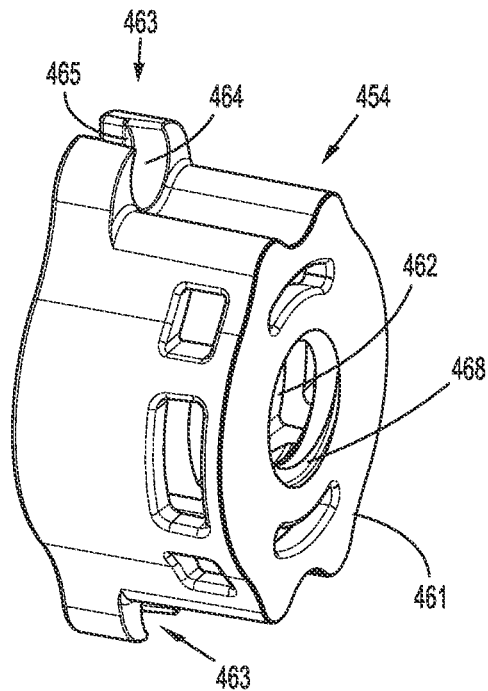
FIG. 8 is an enlarged, front perspective view of the area of detail "8" in FIG. 7.
Figure 9:
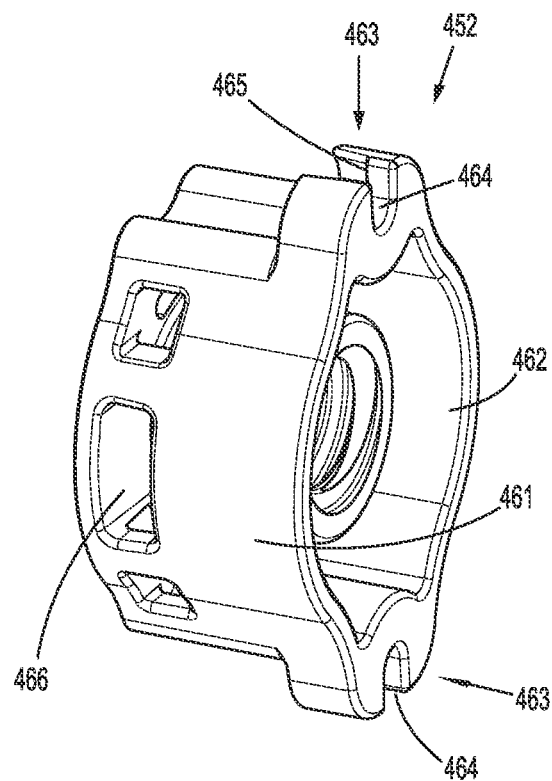
FIG. 9 is an enlarged, rear perspective view of the area of detail "8" in FIG. 7.

With additional reference to FIGS. 8 and 9, spring force assembly 450 includes a proximal hub 452, a distal hub 454, a compression spring 456, and a spring washer 458. Spring force assembly 450 further includes a pair of guide bars 470.

Proximal and distal hubs 452, 454 of spring force assembly 450 may be identical components that are oriented, positioned, and/or coupled to other components differently, thus providing different functionality while reducing the number of different parts required to be manufactured. The features of proximal and distal hubs 452, 454 are detailed below to the extent necessary to facilitate understanding of the present disclosure and, thus, although some features may be detailed with respect to only one of the proximal or distal hub 452, 454 and the function associated therewith, similar features may be provided on the other of the proximal or distal hub 452, 454 without the associated function. Alternatively, proximal and distal hubs 452, 454 may be manufactured as different components.

Proximal and distal hubs 452, 454 of spring force assembly 450 each include a body 461 defining a cavity 462 and a retainer guide 463 extending radially outwardly from opposed sides of body 461. Each retainer guide 463 defines a trough 464 and includes a shoulder 465 extending into the respective trough 464. Proximal and distal hubs 452, 454 are oppositely-oriented relative to one another such that the open ends of cavities 462 face one another and such that the shoulder 465 of each pair of retainer guides 463 of proximal and distal hubs 452, 454 face away from one another.

Figure 18:
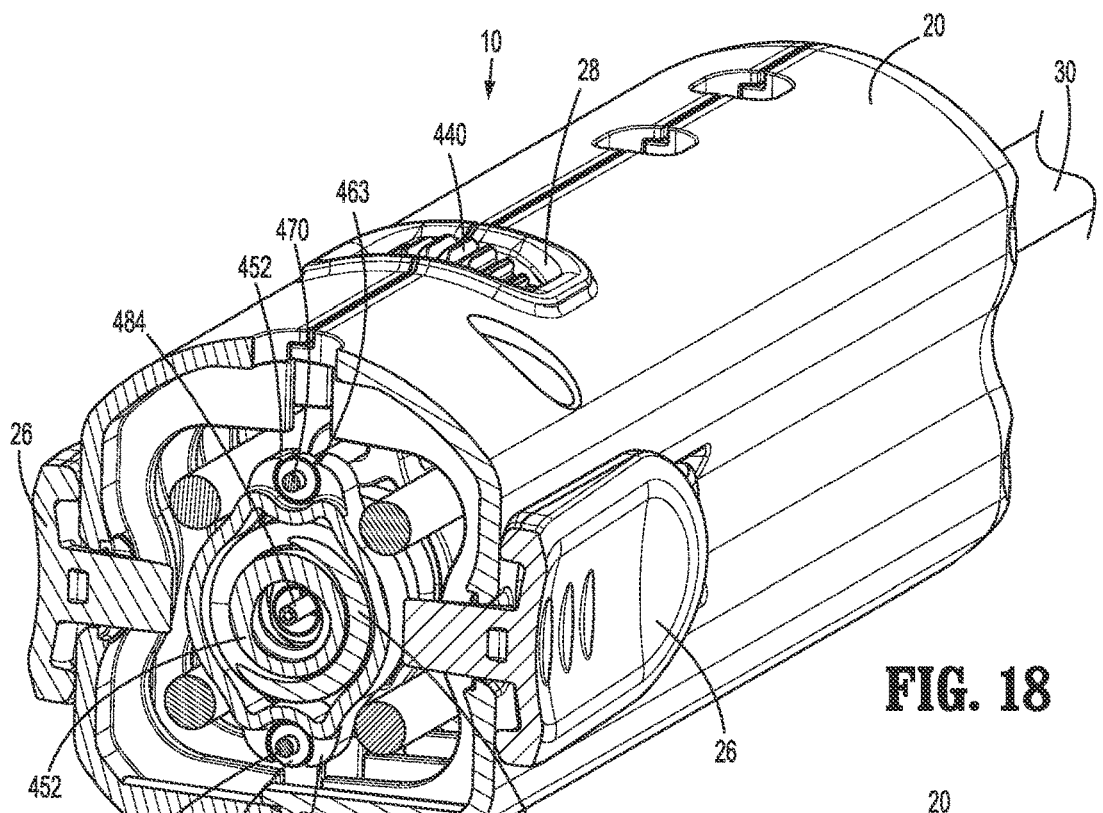
FIG. 18 is a transverse, cross-sectional view taken along section line "18-18" of FIG. 12.

Proximal hub 452 further includes a transverse slot 466 defined therethrough that is configured to receive lock plate 482 of drive rod assembly 480, as detailed below, to fix lock plate 482 and, thus, a proximal end portion of drive rod 484 relative to proximal hub 452 (see FIGS. 18 and 19). Once engaged in this manner, drive rod 484 is locked in position coaxially disposed through proximal hub 452, distal hub 454, compression spring 456, and drive gear 430.

Distal hub 454 defines a threaded central bore 468 through body 461 thereof. Threaded central bore 468 receives lead screw 434 of drive gear 430 therethrough in threaded engagement therewith such that rotation of lead screw 434 drives translation of distal hub 454 longitudinally along lead screw 434.

Compression spring 456 is disposed between proximal and distal hubs 452, 454 with a proximal portion thereof disposed within cavity 461 of proximal hub 452 and a distal portion thereof disposed within cavity 461 of distal hub 462. At least a portion of compression spring 456 is disposed about and/or configured to receive a portion of lead screw 434 of drive gear 430 therethrough. Spring washer 458 is positioned within cavity 461 of proximal hub 452 between proximal hub 452 and compression spring 456, although other configurations are also contemplated.

Each guide bar 470 is slidably received within the troughs 464 of a corresponding pair of retainer guides 463 of proximal and distal hubs 452, 454. Each guide bar 470 includes a pair of spaced-apart rims 472, 474 engaged thereon that are configured to abut shoulders 465 of the respective retainer guides 463, thereby defining a maximum distance between proximal and distal hubs 452, 454. However, proximal and/or distal hubs 452, 454 are permitted to slide along guide bars 470 towards one another, as detailed below.

Figure 5:
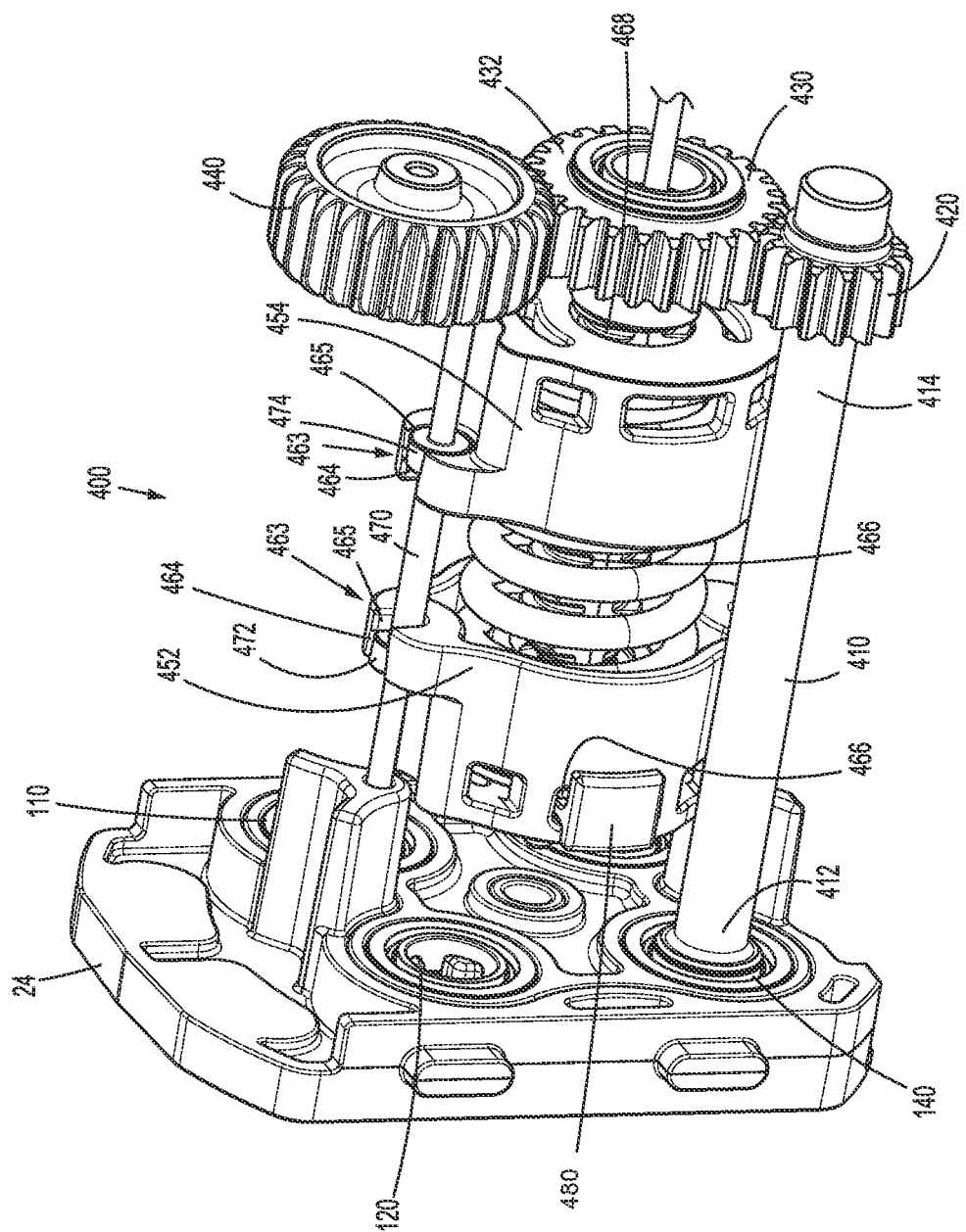
FIG. 5 is a front, perspective view of a jaw drive sub-assembly of the surgical instrument of FIG. 1.
Figure 6:
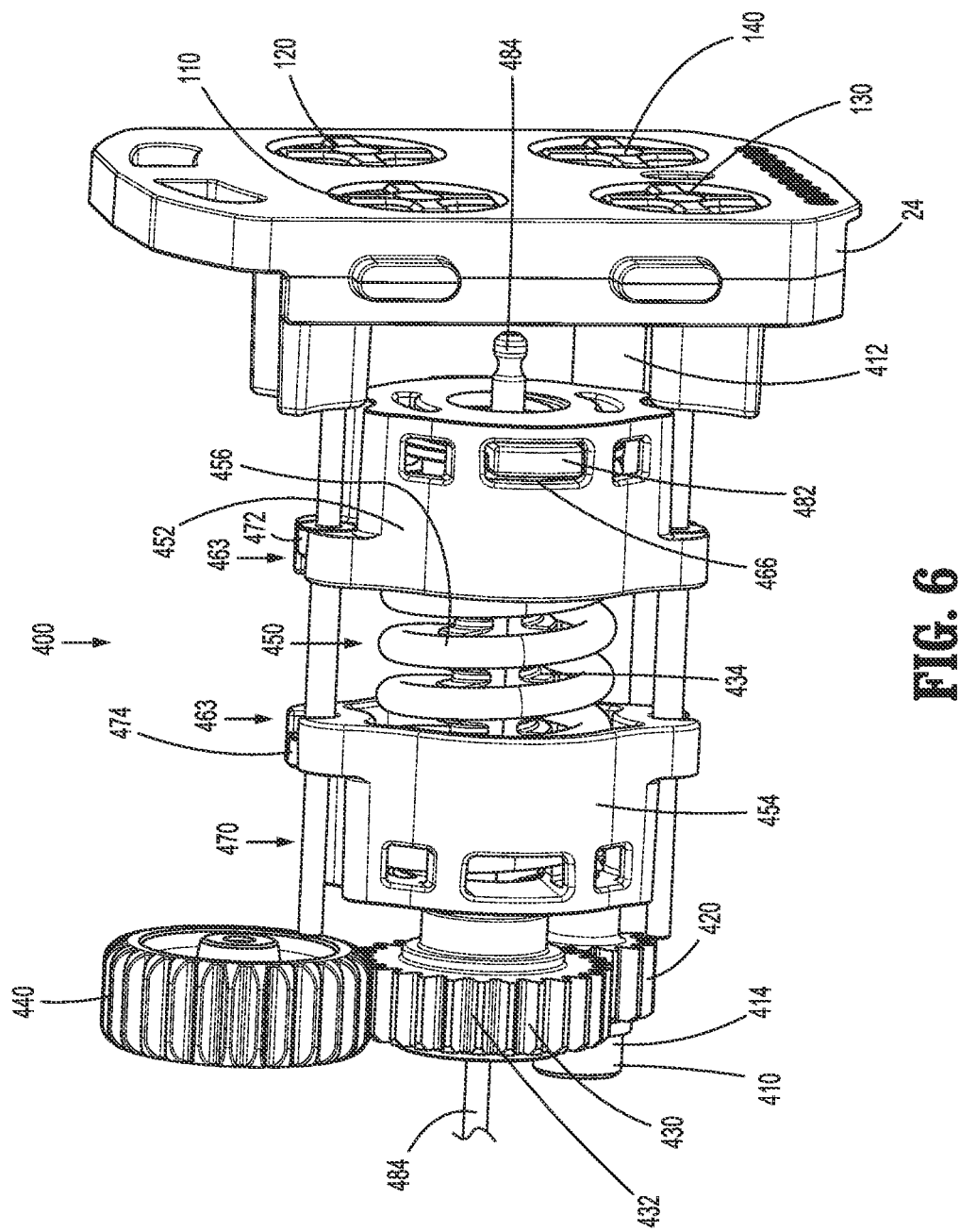
FIG. 6 is a rear, perspective view of the jaw drive sub-assembly of the surgical instrument of FIG. 1.
Figure 7:
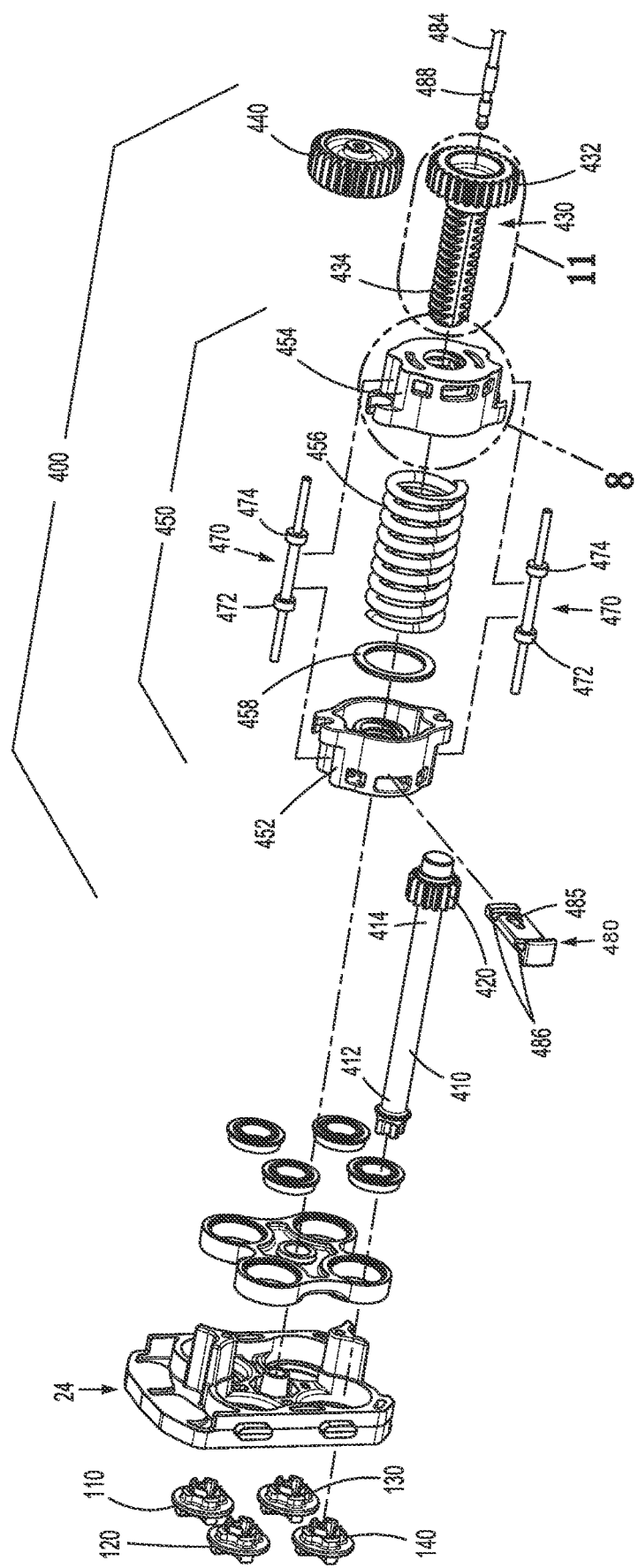
FIG. 7 is an exploded, perspective view of the jaw drive sub-assembly of the surgical instrument of FIG. 1.
Figure 10:
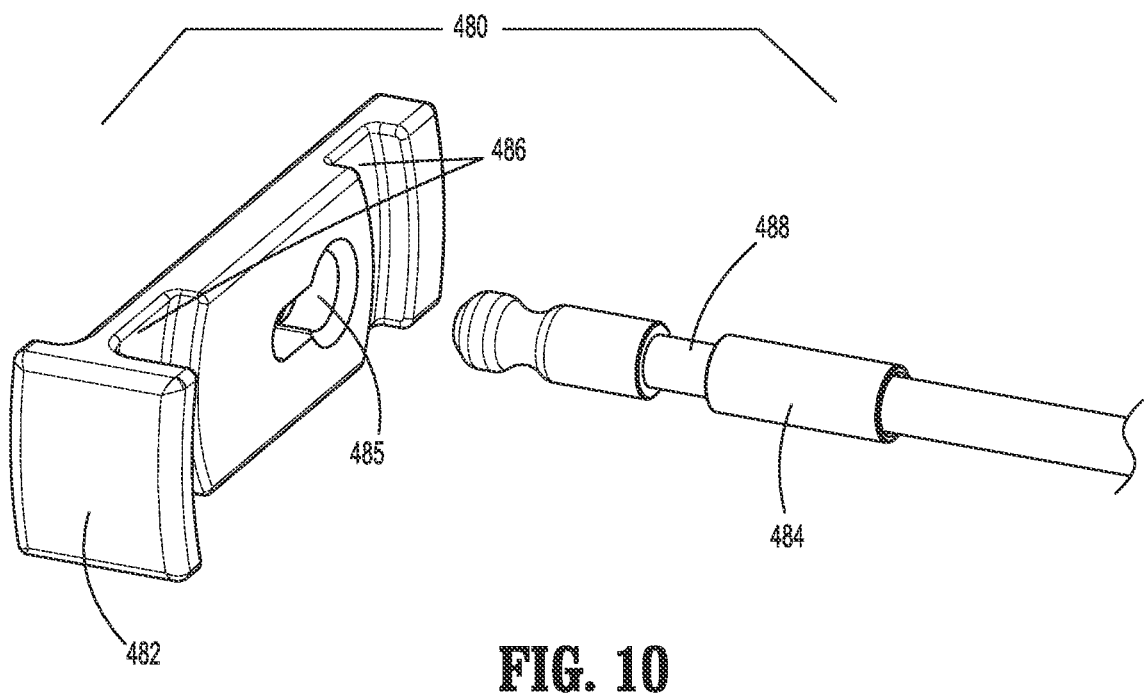
FIG. 10 is an exploded, perspective view illustrating a drive rod and lock plate of the jaw drive sub-assembly of the surgical instrument of FIG. 1.
Figure 19:
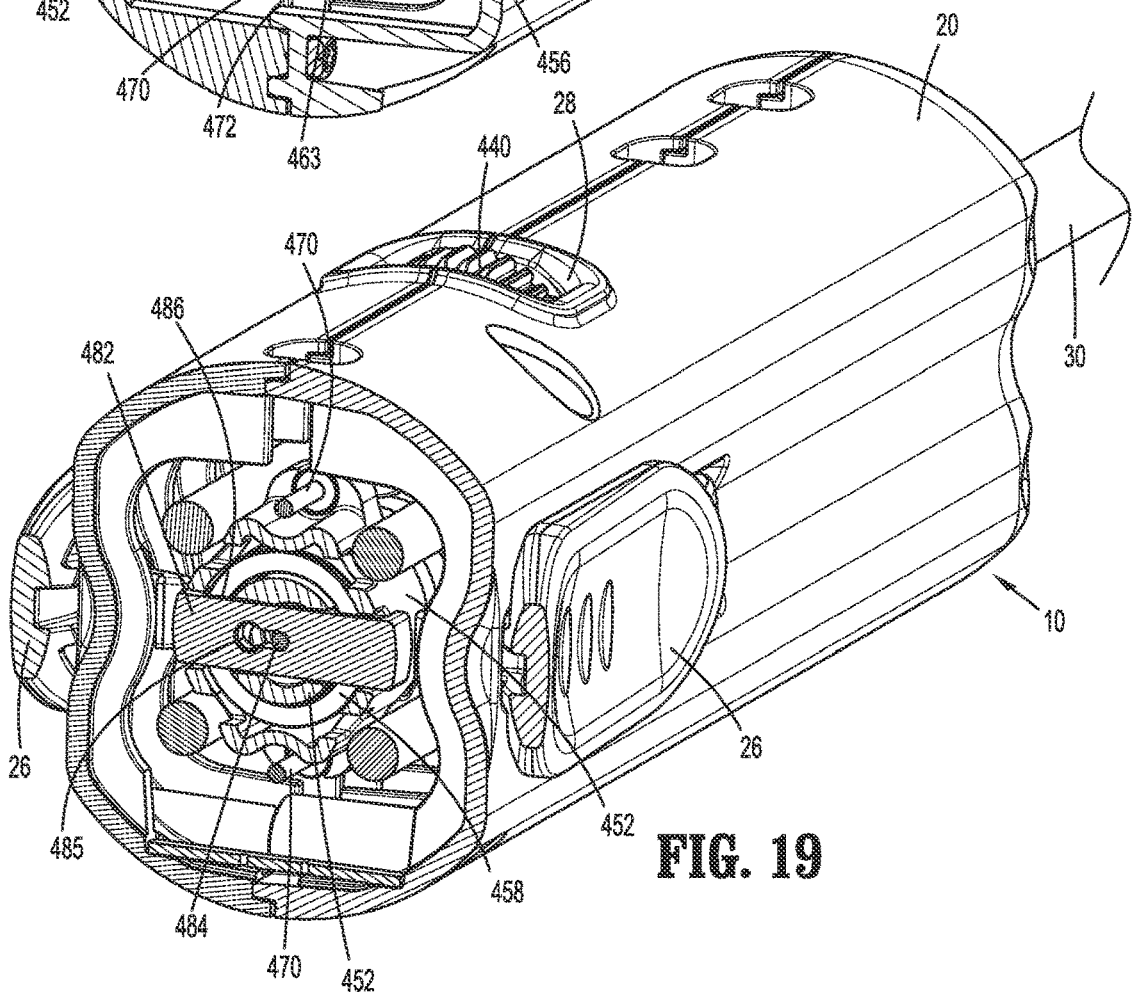
FIG. 19 is a transverse, cross-sectional view taken along section line "19-19" of FIG. 12.

Referring to FIGS. 10 and 19, in conjunction with FIGS. 5-7, drive rod assembly 480 includes lock plate 482 and drive rod 484. Lock plate 482 defines a central keyhole 485 and a pair of slots 486, e.g., arcuate slots, defined on a distal face of lock plate 482 on either side of central keyhole 485. Lock plate 482 is configured for insertion through transverse slot 466 of proximal hub 452 and, once installed therein, portions of spring washer 458 are configured for receipt within slots 486 to secure lock plate 482 in engagement within proximal hub 452. Spring washer 458 is maintained in position within slots 486 under the bias of compression spring 456 which, at the maximum distance between proximal and distal hubs 452, 454 (as set by rims 472, 474 of guide bars 470 and shoulders 465 of retainer guides 463), is pre-compressed.

Drive rod 484, as noted above, includes a distal end portion operably coupled to cam-slot assembly 52 of end effector assembly 40 (FIG. 1). Drive rod 484 extends proximally through shaft 30, housing 20, and gearbox assembly 100 (see FIGS. 1-3) and is engaged within lock plate 482 at a proximal end portion of drive rod 484. More specifically, drive rod 484 defines a waist 488 towards the proximal end thereof that is configured to lock in engagement within central keyhole 485 of lock plate 482, e.g., via longitudinal translation of drive rod 484 into central keyhole 485 until waist 488 is aligned with central keyhole 485, followed by transverse movement of drive rod 484 relative to lock plate 482, to thereby fix the proximal end portion of drive rod 484 relative to lock plate 482 and, thus, relative to proximal hub 452 due to the engagement of lock plate 482 within proximal hub 452.

Turning to FIGS. 3, 12-15, and 17, knife drive sub-assembly 300 includes an input shaft 310, an input gear 320, a central gear 330 defining external threading and internal threading, and a lead screw 340. Input shaft 310 extends parallel and offset relative to input shaft 410 and includes a proximal end portion 312 operably coupled to third input 130 of gearbox assembly 100 (FIGS. 2A and 2B) and a distal end portion 314 having input gear 320 engaged thereon such that rotational input provided to third input 130 drives rotation of input shaft 310 to, thereby, drive rotation of input gear 320. Input gear 320 is disposed in meshed engagement with the external threading of central gear 330. Central gear 330 is coaxial with and positioned distally of drive gear 430.

Lead screw 340 extends through central gear 330 and is threadingly engaged with the internal threading thereof such that rotation of central gear 330, e.g., in response to a rotational input provide to third input 130, translates lead screw 340. Lead screw 340 is fixedly engaged about a proximal end portion of knife tube 62 such that translation of lead screw 340 translates knife tube 62, e.g., to thereby translate the knife blade (not shown) between jaw members 42, 44 (FIG. 1). Lead screw 340 and knife tube 62 are coaxially disposed about drive rod 484.

Referring to FIGS. 5-7 and 20-23, in use, jaw members 42, 44 are initially disposed in the spaced-apart position (FIG. 20) and, correspondingly, proximal and distal hubs 452, 454 are disposed in a distal-most position such drive rod 484 is disposed in a distal-most position (see FIGS. 12-15). Further, in this position, compression spring 456 is disposed in a least-compressed condition; although, as noted above, even in the least-compressed condition, compression spring 456 is partially compressed due to the retention of compression spring 456 in a pre-compressed configuration between proximal and distal hubs 452, 454.

Figure 20:
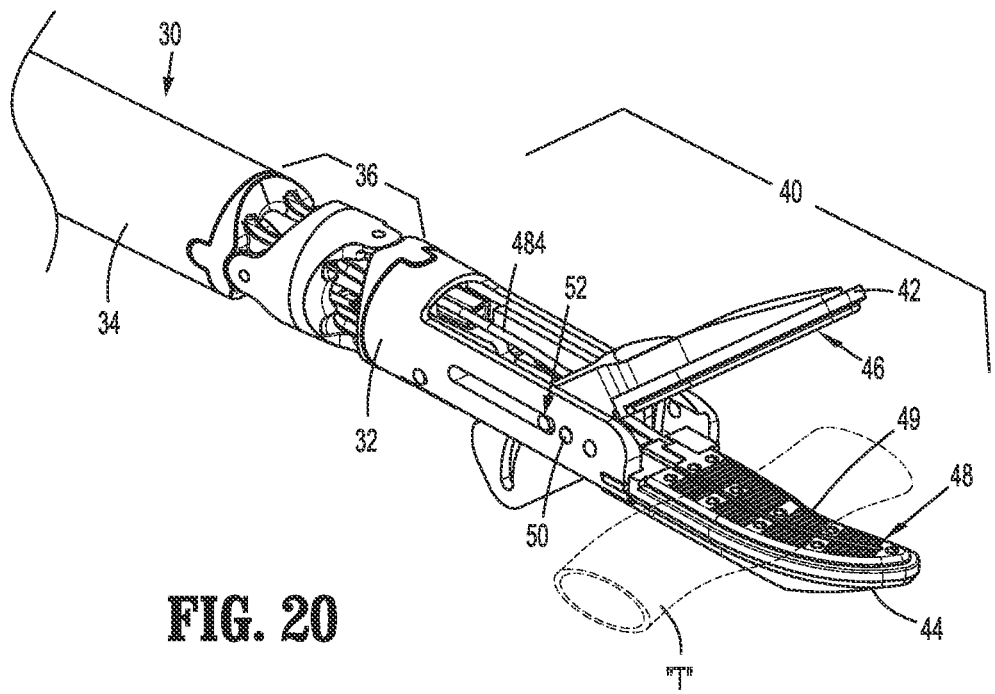
FIG. 20 is a perspective view of a distal portion of the surgical instrument of FIG. 1 with the end effector assembly disposed in an open position.
Figure 21:
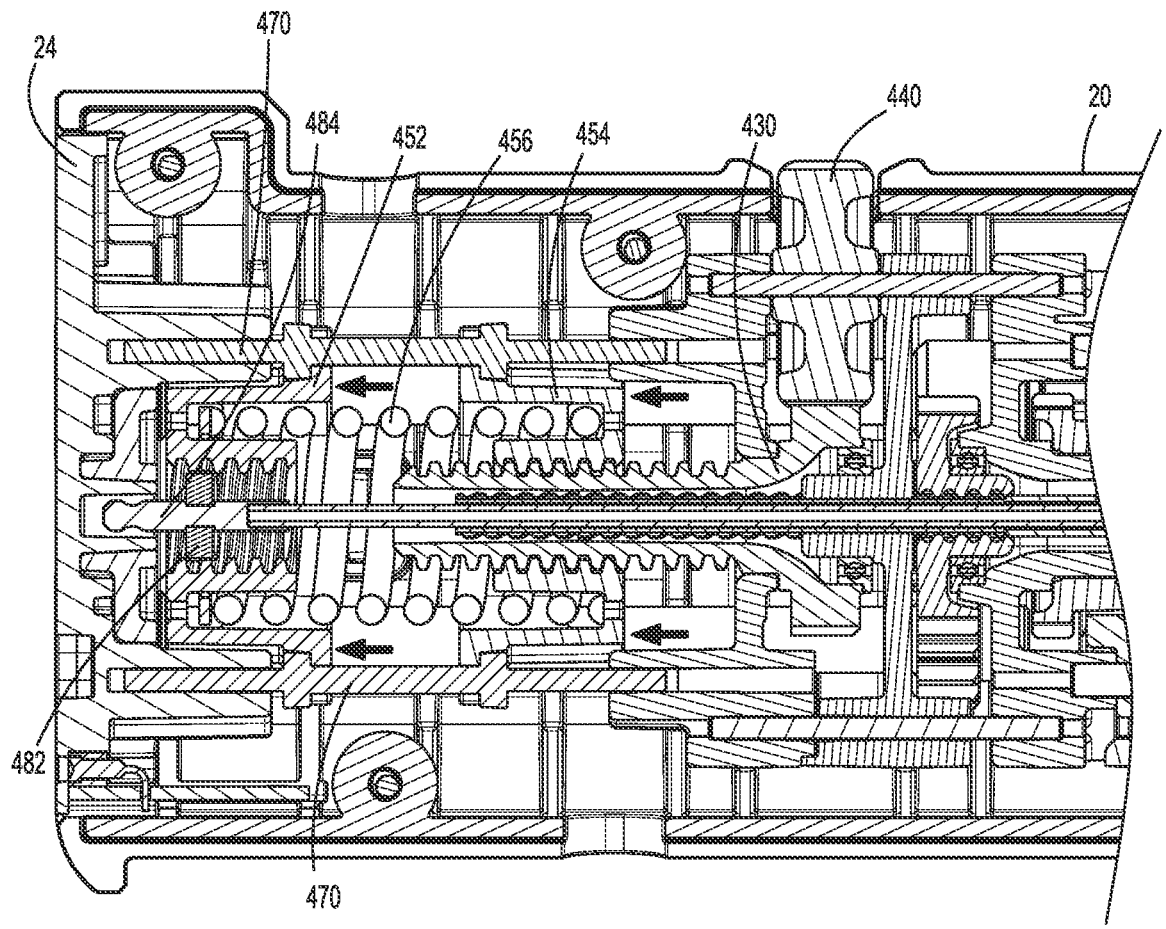
FIG. 21 is a longitudinal, cross-sectional view of another proximal portion of the surgical instrument of FIG. 1 illustrating the jaw drive sub-assembly transitioning the end effector assembly from the open position towards a closed position.

In response to an input to close end effector assembly 40, e.g., rotational input to fourth input 140 or a manual input to rotation wheel 440, drive shaft 410 is rotated to thereby rotate input gear 420 which, in turn, rotates drive gear 430 such that distal hub 454 is translated proximally towards proximal hub 452 (see FIG. 21). With reference to FIG. 21, proximal translation of distal hub 454 urges distal hub 454 against compression spring 456. Initially, where forces resisting approximation of jaw members 42, 44 are below a threshold corresponding to the spring value of compression spring 456, the closure force applied by jaw members 42, 44 is relatively low such that the urging of distal hub 454 proximally against compression spring 456 urges compression spring 456 proximally which, in turn, urges lock plate 482 and, thus, drive rod 484 proximally to pivot jaw member 42 relative to jaw member 44 from the spaced-apart position towards the approximated position to grasp tissue "T" therebetween (FIGS. 20 and 22).

Referring to FIGS. 5-7, 22, and 23, upon further approximation of jaw members 42, 44 to grasp tissue "T" therebetween, the forces resisting approximation of jaw members 42, 44, e.g., tissue "T" resisting compression, may reach the threshold and, thus the closure force applied by jaw members 42, 44 may reach a corresponding threshold. In order to maintain the closure force applied by jaw members 42, 44 within a closure force range such as, for example, from about 3 kg/cm$^2$ to about 16 kg/cm$^2$, application of further closure force by jaw members 42, 44 is inhibited beyond this point despite further rotational input to fourth input 140.

Figure 23:
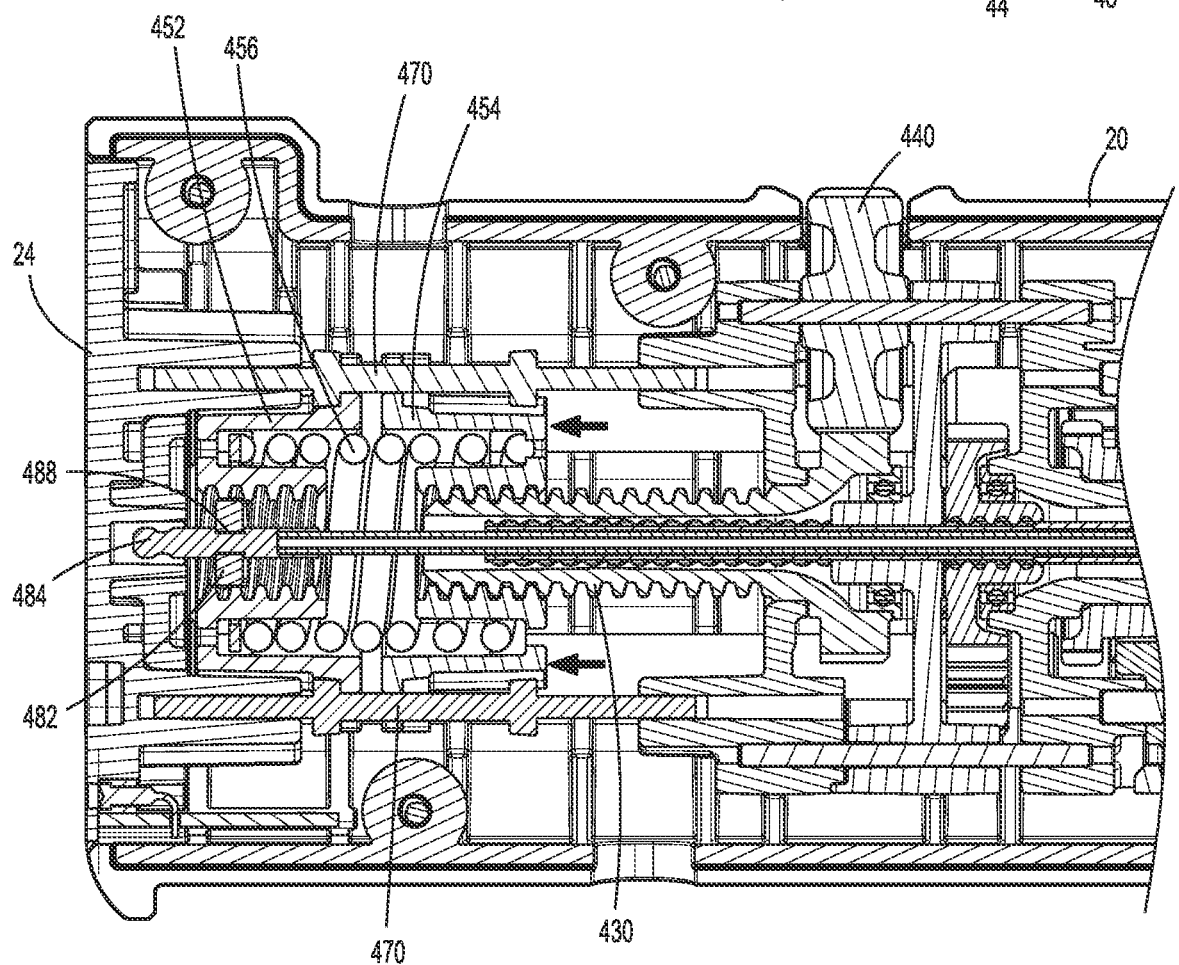
FIG. 23 is a longitudinal, cross-sectional view of the proximal portion of the surgical instrument of FIG. 21 illustrating the jaw drive sub-assembly with the end effector assembly in the closed position.

More specifically, and with reference to FIG. 23, once the threshold has been reached, further rotational input to fourth input 140 rotates drive shaft 410, input gear 420, and drive gear 430 to translate distal hub 454 further proximally into compression spring 456. However, rather than compression spring 456 urging proximal hub 452 further proximally to continue approximation of jaw members 42, 44 and increase the closure force applied therebetween, compression spring 456 is compressed, enabling proximal hub 452 and, thus, drive rod 484 to remain in position, thus inhibiting application of additional closure force between jaw members 42, 44.

Figure 14:
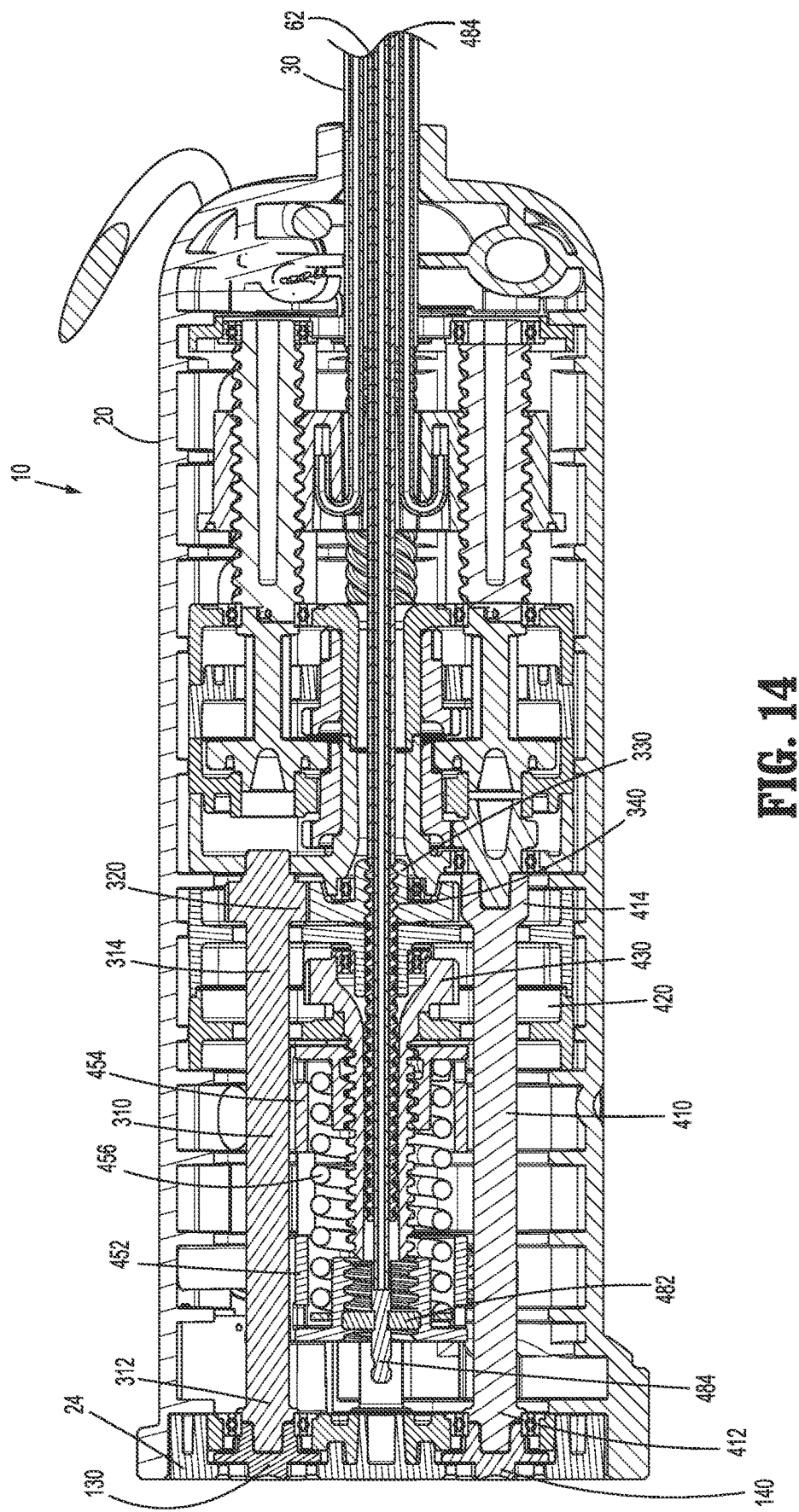
FIG. 14 is a transverse, cross-sectional view taken along section line "14-14" of FIG. 3.
Figure 15:
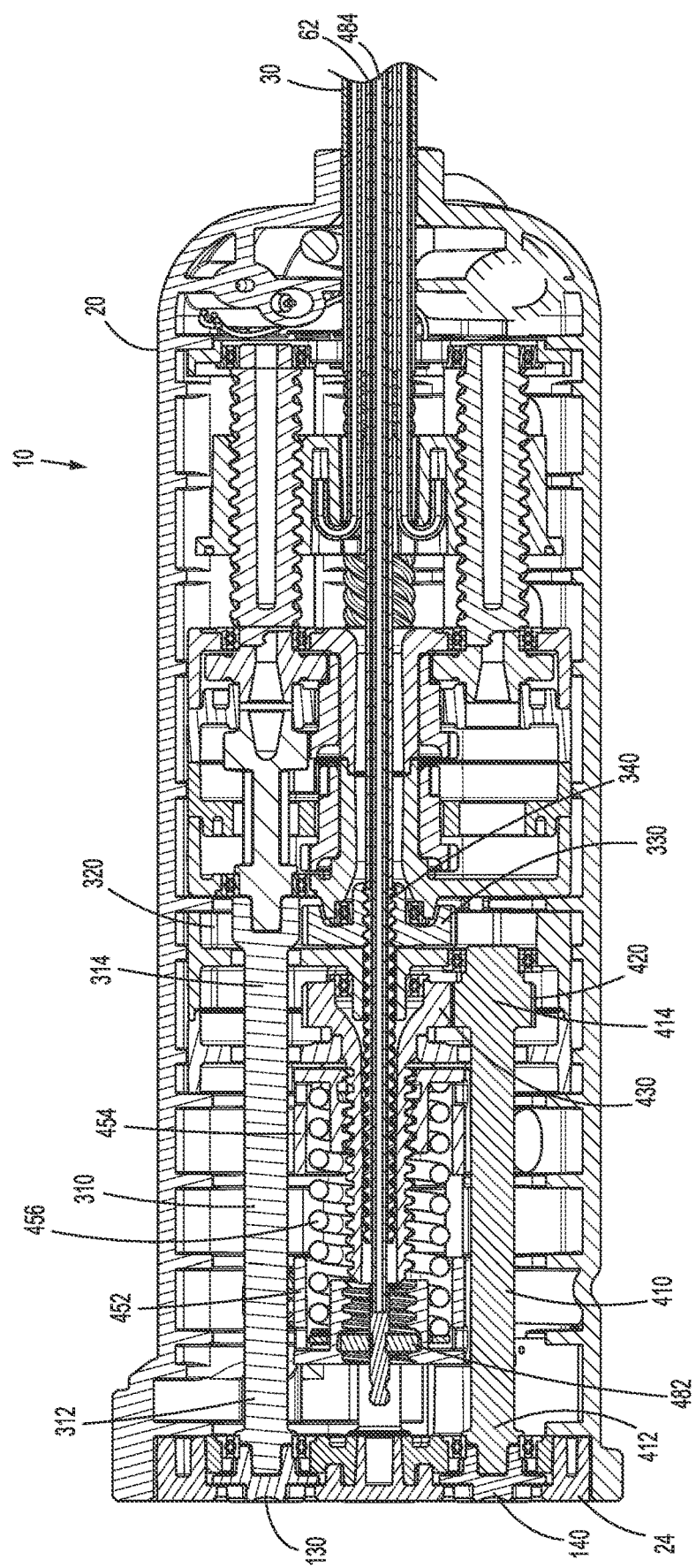
FIG. 15 is a transverse, cross-sectional view taken along section line "15-15" of FIG. 3.
Figure 16:
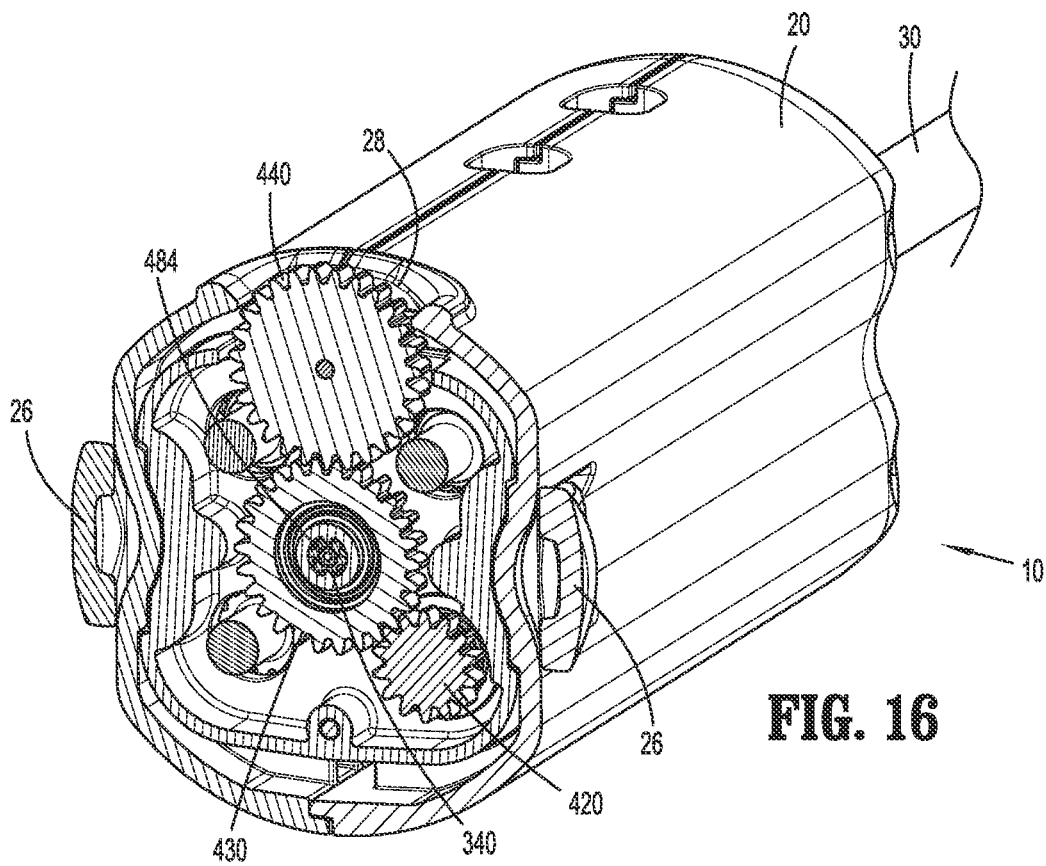
FIG. 16 is a transverse, cross-sectional view taken along section line "16-16" of FIG. 12.
Figure 17:
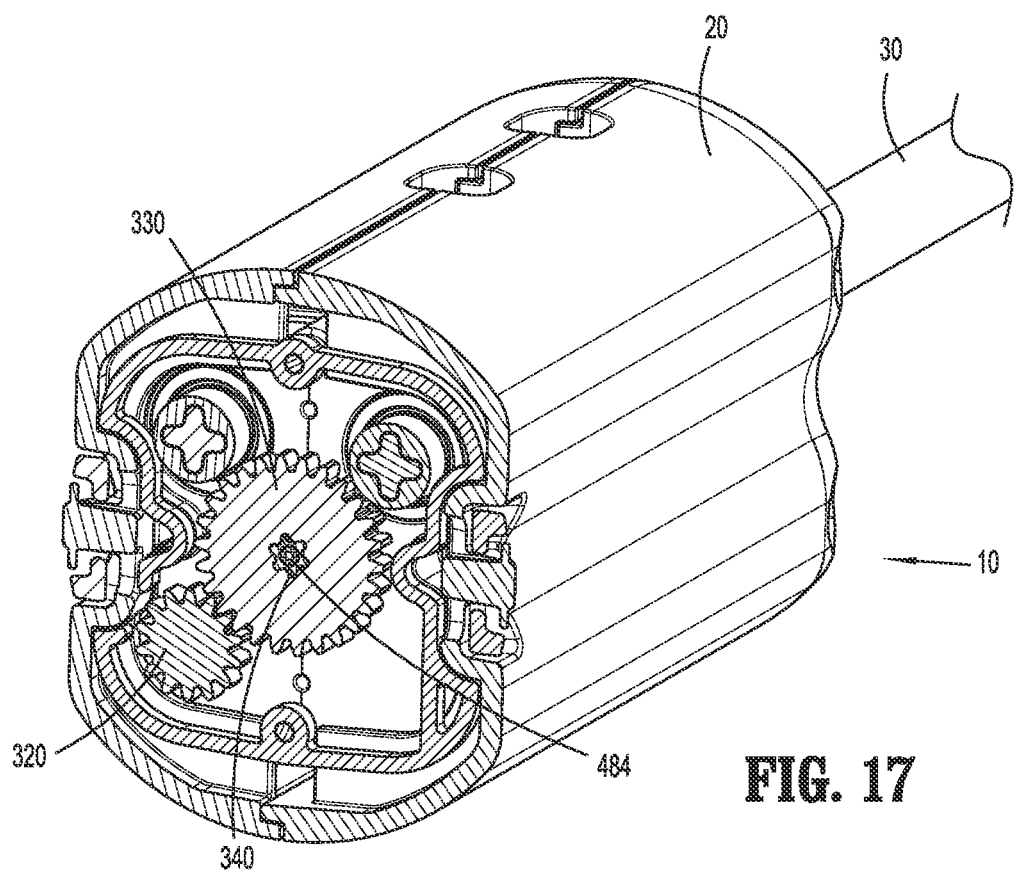
FIG. 17 is a transverse, cross-sectional view taken along section line "17-17" of FIG. 12.
Figure 22:
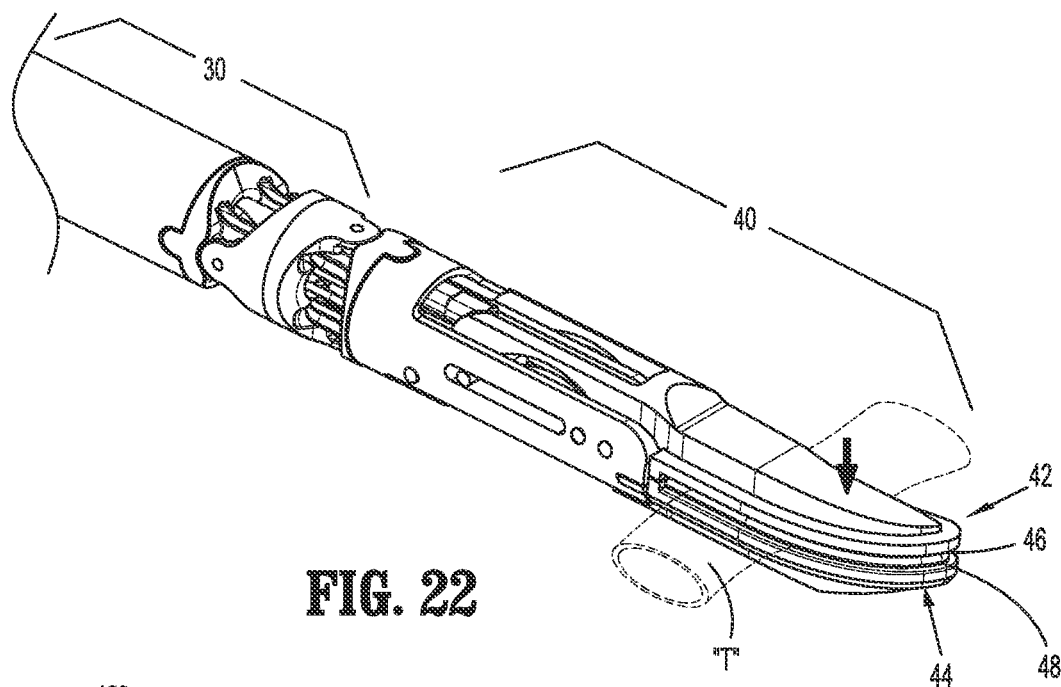
FIG. 22 is a perspective view of the distal portion of the surgical instrument of FIG. 1 with the end effector assembly disposed in the closed position.

Referring to FIG. 22, with tissue "T" grasped between jaw members 42, 44 under an appropriate closure force, energy may be supplied to jaw members 42, 44 to treat, e.g., seal tissue "T." Thereafter, the knife blade (not shown) may be advanced between jaw members 42, 44 to cut the treated tissue "T." With additional reference to FIGS. 14 and 17, in order to advance the knife blade (not shown), a rotational input is provided to input 130 to drive rotation of input shaft 310, input gear 320, and central gear 330, thereby translating lead screw 340 distally such that knife tube 62 is likewise translated distally to advance the knife blade (not shown) between jaw members 42, 44 to cut the treated tissue "T." Alternatively, tissue "T" may be cut without first treating the tissue "T" and/or tissue "T" may be treated without subsequent cutting.

Once tissue "T" is cut, an opposite rotation input is provided to input 130 to return the knife blade (not shown) to its initial position proximally of body portions 43b, 45b of jaw members 42, 44 (see FIG. 1). Thereafter, an opposite input is provided to input 140 (or rotation wheel 440) to return jaw members 42, 44 back towards the spaced-apart position to release the sealed and/or cut tissue.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A gearbox assembly for a surgical instrument, comprising:
    a lead screw configured to receive a rotational input to rotate the lead screw;
    a first hub threadingly engaged with the lead screw such that rotation of the lead screw translates the first hub, the first hub including a first retainer guide;
    a second hub including a second retainer guide;
    a guide bar extending through the first and second retainer guides of the first and second hubs, respectively, to inhibit rotation of the first and second hubs;
    a drive rod engaged with the second hub, wherein the first hub is slidably disposed about the drive rod; and
    a spring including a first end portion contacting the first hub and a second end portion contacting the second hub, the drive rod extending through at least a portion of the spring,
    wherein, when a force acting against translation of the drive rod is below a threshold, translation of the first hub translates the spring to translate the second hub and thereby translate the drive rod, and wherein, when the force acting against translation of the drive rod is equal to or above the threshold, translation of the first hub compress the first end portion of the spring towards the second end portion of the spring such that the second end portion of the spring, the second hub, and, thus, the drive rod are maintained in position.

2. The gearbox assembly according to claim 1, further comprising an input coupler coupled to the lead screw, wherein the input coupler is rotatable to thereby provide the rotational input to the lead screw.

3. The gearbox assembly according to claim 2, wherein at least one additional gear couples the input coupler to the lead screw.

4. The gearbox assembly according to claim 1, wherein the first hub is a distal hub, the second hub is a proximal hub, the first end portion of the spring is a distal end portion of the spring, and the second end portion of the spring is a proximal end portion of the spring.

5. The gearbox assembly according to claim 1, wherein the drive rod extends coaxially through each of: the first hub, the second hub, and the spring.

6. The gearbox assembly according to claim 1, wherein the guide bar and each of the first and second retainer guides are configured for relative slidable motion.

7. The gearbox assembly according to claim 1, wherein the drive rod is engaged with the second hub via a lock plate defining a keyhole.

8. A surgical instrument, comprising:
a housing;
an end effector assembly distally spaced from the housing; and
a gearbox assembly disposed within the housing, the gearbox assembly including:
a first hub configured to translate through the housing in response to receipt of a rotational input into the housing, the first hub including a first retainer guide;
a second hub including a second retainer guide;
a guide bar coupled to the first and second retainer guides to inhibit rotation of the first and second hubs;
a drive rod engaged with the second hub at a proximal end portion of the drive rod and engaged with the end effector assembly at a distal end portion of the drive rod; and
a spring coupled between the first and second hubs, the drive rod extending through at least a portion of the spring,
wherein, when a force acting against the end effector assembly is below a threshold, translation of the first hub translates the spring to translate the second hub and thereby translate the drive rod, and wherein, when the force acting against the end effector assembly is equal to or above the threshold, translation of the first hub compresses the spring such that the second hub and, thus, the drive rod are maintained in position.

9. The surgical instrument according to claim 8, wherein the gearbox assembly further includes a lead screw, wherein the first hub is threadingly engaged with the lead screw, and wherein the rotational input into the housing rotates the lead screw to thereby translate the first hub.

10. The surgical instrument according to claim 9, further comprising an input coupler extending through the housing, the input coupler configured to provide the rotational input into the housing.

11. The surgical instrument according to claim 8, wherein the first hub is a distal hub, the second hub is a proximal hub, and wherein the translation of the drive rod is proximal translation of the drive rod.

12. The surgical instrument according to claim 8, wherein the guide bar and each of the first and second retainer guides are configured for relative slidable motion.

13. The surgical instrument according to claim 8, wherein the guide bar extends longitudinally through the housing.

14. A surgical instrument, comprising:
a housing;
a shaft extending distally from the housing, the shaft including an articulating portion;
an end effector assembly extending distally from the shaft, the end effector assembly including first and second jaw members, at least one of the first or second jaw members movable relative to another of the first or second jaw members from a spaced-apart position to an approximated position to grasp tissue between the first and second jaw members; and
a gearbox assembly disposed within the housing, the gearbox assembly including:
an articulation sub-assembly, the articulation sub-assembly including a plurality of lead screws operably coupled to the articulating section of the shaft via a plurality of articulation cables, the articulation sub-assembly configured to articulate the end effector assembly relative to the housing in response to receipt of at least one first rotational input into the housing; and
a jaw drive sub-assembly, including:
a first hub positioned proximally of the articulation sub-assembly and configured to translate through the housing in response to receipt of a second rotational input into the housing;
a second hub positioned proximally of the first hub;
a guide bar coupled to the first and second hubs and configured to inhibit rotation of the first and second hubs;
a drive rod engaged with the second hub at a proximal end portion of the drive rod, the drive rod extending through the articulation sub-assembly and the shaft and engaged with the at least one of the first or second jaw members of the end effector assembly at a distal end portion of the drive rod; and
a spring coupled between the first and second hubs and configured to selectively transfer motion from the first hub to the second hub and the drive rod in response to translation of the first hub.

15. The surgical instrument according to claim 14, wherein, when a force between the first and second jaw members is below a threshold, the spring is configured to transfer motion from the first hub to the second hub in response to translation of the first hub such that the second hub and the drive rod are translated in response to translation of the first hub.

16. The surgical instrument according to claim 15, wherein, when the force between the first and second jaw members is equal to or above the threshold, the spring is configured to absorb the motion of the first hub in response to translation of the first hub such that the second hub and the drive rod are maintained in position in response to translation of the first hub.

17. The surgical instrument according to claim 14, wherein the jaw-drive sub-assembly further includes a jaw-drive lead screw, wherein the first hub is threadingly engaged with the jaw-drive lead screw, and wherein the second rotational input into the housing rotates the jaw-drive lead screw to thereby translate the first hub.

18. The surgical instrument according to claim 14, further comprising a first input coupler and a second input coupler extending through the housing, the first input coupler configured to provide the at least one first rotational input into the housing and the second input coupler configured to provide the second rotational input into the housing.

19. The surgical instrument according to claim 14, wherein the guide bar and each of the first and second retainer guides are configured for relative slidable motion.

20. The surgical instrument according to claim 14, wherein the drive rod extends through at least a portion of the spring.

* * * * *